(12) United States Patent
Inadome et al.

(10) Patent No.: US 9,474,845 B2
(45) Date of Patent: Oct. 25, 2016

(54) CELL REMOVAL METHOD, CELL REMOVAL SYSTEM, AND WHITE BLOOD CELL REMOVAL METHOD

(75) Inventors: Shuichiro Inadome, Tokyo (JP); Nobukazu Shimada, Tokyo (JP); Tomohisa Yokomizo, Tokyo (JP)

(73) Assignee: ASAHI KASEI MEDICAL CO. LTD., Tokyo (JP)

( * ) Notice: Subject to any disclaimer, the term of this patent is extended or adjusted under 35 U.S.C. 154(b) by 767 days.

(21) Appl. No.: 13/635,194

(22) PCT Filed: Mar. 22, 2011

(86) PCT No.: PCT/JP2011/056751
§ 371 (c)(1),
(2), (4) Date: Sep. 14, 2012

(87) PCT Pub. No.: WO2011/115291
PCT Pub. Date: Sep. 22, 2011

(65) Prior Publication Data
US 2013/0005558 A1    Jan. 3, 2013

(30) Foreign Application Priority Data

Mar. 19, 2010    (JP) .................................. 2010-064452

(51) Int. Cl.
| | | |
|---|---|---|
| *A61M 1/36* | (2006.01) | |
| *A61M 1/02* | (2006.01) | |
| *A61M 1/34* | (2006.01) | |

(52) U.S. Cl.
CPC ......... *A61M 1/3696* (2014.02); *A61M 1/0209* (2013.01); *A61M 1/0218* (2014.02); *A61M 1/34* (2013.01); *A61M 1/3693* (2013.01); *A61M 2202/0439* (2013.01)

(58) Field of Classification Search
CPC .. A61M 1/0209; A61M 1/34; A61M 1/3693; A61M 1/0218; A61M 1/3616; A61M 2202/0439; B04B 5/0442
See application file for complete search history.

(56) References Cited

U.S. PATENT DOCUMENTS 3,928,139 A    12/1975  Dorn
5,836,934 A *  11/1998  Beshel .......................... 604/410
(Continued)

FOREIGN PATENT DOCUMENTS

EP    0852151 A1    7/1996
EP    1582228 A1    10/2005
(Continued)

OTHER PUBLICATIONS

Search report from International Application No. PCT/JP2011/056751, mail date is May 17, 2011.
(Continued)

*Primary Examiner* — Timothy Cleveland
(74) *Attorney, Agent, or Firm* — Greenblum & Bernstein, P.L.C.

(57) ABSTRACT

In the removal of white blood cells from blood, the efficiency of white blood cell removal by a filter is improved. Centrifugal force is applied to blood placed in a blood bag by centrifugal separation to form a plurality of separation layers having a concentration gradient of white blood cells. The separation layers are passed through a filter in ascending order of white blood cell concentration to remove the white blood cells from the separation layers. The separation layers from which the white blood cells have been removed are received in a first blood component bag.

6 Claims, 9 Drawing Sheets

(56) References Cited

U.S. PATENT DOCUMENTS

| | | | |
|---|---|---|---|
| 5,954,971 A * | 9/1999 | Pages et al. | 210/739 |
| 2004/0200775 A1 | 10/2004 | Fukuda et al. | |
| 2007/0282242 A1 | 12/2007 | Gibbs et al. | |
| 2008/0147240 A1 * | 6/2008 | Hudock et al. | 422/72 |

FOREIGN PATENT DOCUMENTS

| | | |
|---|---|---|
| EP | 2548590 A1 | 1/2013 |
| JP | 2000-334034 | 12/2000 |
| JP | 2002-320669 | 11/2002 |
| JP | 2009-90136 | 4/2009 |
| JP | 2009-268917 | 11/2009 |
| WO | 02/087660 | 11/2002 |
| WO | 2008/079611 | 7/2008 |
| WO | 2008-105972 A1 | 9/2008 |

OTHER PUBLICATIONS

International Preliminary Report on Patentability for International Application No. PCT/JP2011/056751, mail date is May 17, 2011.
European search report issued with respect to application No. 15150330.7, mail date is Apr. 22, 2015.
Extended European Search Report in Application No. 16157832.3, dated May 11, 2016.

* cited by examiner

CELL REMOVAL METHOD, CELL REMOVAL SYSTEM, AND WHITE BLOOD CELL REMOVAL METHOD

BACKGROUND

The present invention relates to a cell removal method, a cell removal system, and a white blood cell removal method.

In order to perform blood component transfusion, for example, it is necessary to separate blood components such as packed red blood cell components or plasma components from blood to produce a blood component product. A blood component product is produced using, for example, a system that can be mounted on a centrifugal separator. Such a system includes, for example, a blood collection bag that receives blood collected from the human body, a blood bag, a blood component bag that receives separated blood components, a tube that connects them, and the like (see Patent Literature 1).

In the production of a blood component product, for example, blood in the blood collection bag is passed through a filter using the difference in gravity to remove white blood cells that are a pathogenic substance, and then received in the blood bag. Subsequently, the blood component production system is mounted on a centrifugal separator. Using the centrifugal separator, blood in the blood bag is separated by centrifugation into a plasma component layer and a red blood cell component layer, for example, according to the difference in cell concentration. Subsequently, for example, the system is mounted on an apheresis system, and the plasma component layer in the blood bag is pressed out and received in the blood component bag to produce a plasma product.

In addition, the red blood cell component layer remaining in the blood bag is pressed out by the apheresis system and received in another blood component bag to produce a red blood cell product.

Patent Literature 1: Patent Publication JP-A-2009-90136
Patent Literature 2: Patent Publication JP-A-2002-320669

Incidentally, for example, in the production of a blood component product mentioned above, in order to more reliably prevent side effects of blood component transfusion caused by white blood cells, etc., it is necessary to further increase the efficiency of white blood cell removal by a filter. In addition, by increasing the efficiency of white blood cell removal by a filter, the filter can be reduced in size. By reducing the filter size, the amount of useful components caught by the filter and wasted, such as red blood cells, can be reduced.

SUMMARY

The present invention has been accomplished against the above background. An object of the present invention is to increase the efficiency of cell removal by a filter in the removal of predetermined cells such as white blood cells from a body fluid such as blood.

The present invention for achieving the above object is a cell removal method for removing predetermined cells from a body fluid. The method includes: applying centrifugal force to a body fluid placed in a first bag by centrifugal separation to form separation layers having a concentration gradient of the predetermined cells; passing the separation layers through a filter in ascending order of the concentration of the predetermined cells according to the concentration gradient of the predetermined cells to remove the predetermined cells from the separation layers; and receiving the separation layers from which the predetermined cells have been removed in a second bag. Incidentally, the concentration of predetermined cells herein is mass concentration.

According to the present invention, by centrifugal force, separation layers having a concentration gradient of predetermined cells are formed, and the separation layers having a cell concentration gradient are passed through a filter in ascending order of the concentration of the predetermined cells. Thus, the separation layer having the highest concentration of the predetermined cells can be the last to pass through the filter. Accordingly, filtration can be continued while suppressing a decrease in the predetermined cell removal performance caused by a temporary decrease in the number of adsorption sites accompanying the progress of filtration, which is seen in the case where a body fluid component having a uniform cell concentration is passed through a filter. As a result, as compared with such a case, the efficiency of predetermined cell removal by a filter can be increased.

It is also possible that the separation layers are passed through the filter using the centrifugal force by the centrifugal separation. In such a case, the separation layers can be passed through the filter while reliably maintaining the separated state of the separation layers. In addition, the separation layers can be passed through the filter during or immediately after the centrifugal separation that separates the body fluid into the separation layers, whereby the time of the cell removal process can be shortened. In addition, the need for a special device for passing a body fluid component through a filter is eliminated, whereby the cost of the cell removal process can be reduced.

It is also possible that when the separation layers are passed through the filter, a passing rate may be changed according to the concentration of the predetermined cells. In such a case, according to the cell concentration of each separation layer, the separation layers can be passed at an optimal rate, whereby the performance of the filter is effectively exhibited, and the efficiency of predetermined cell removal by the filter can be improved.

It is also possible that a body fluid component produced by removing the predetermined cells from the separation layers is received in the second bag, and that a preservation liquid for preserving the body fluid component may be added to the separation layers before being passed through the filter. In such a case, the preservation liquid can be added in the process of removing the predetermined cells. Therefore, there is no need for the process of separately adding a preservation liquid. In addition, the separation layers are diluted with the preservation liquid and thus more easily pass through the filter. Therefore, the burden on the filter can be reduced, prolonging the life of the filter.

It is also possible that an additional separation layer other than the separation layers that is separated by the centrifugal force described above is received in a third bag separately from the separation layers described above.

The predetermined cells may be pathogens. In addition, it is also possible that the body fluid is blood, the predetermined cells are white blood cells, and the predetermined cells are removed from the separation layers to produce a blood component containing red blood cells as a main component.

The present invention from another point of view is a cell removal system that is mounted on a centrifugal separator and removes predetermined cells from a body fluid. The cell removal system includes: a body fluid bag that receives a body fluid; a first body fluid component bag that receives a first body fluid component having a relatively high cell concentration in the body fluid; a second body fluid component bag that receives a second body fluid component having a relatively low cell concentration in the body fluid; a first channel that connects the first body fluid component bag and the body fluid bag; a second channel that connects the second body fluid component bag and the body fluid bag; a filter that is provided in the first channel and removes predetermined cells from a body fluid component passing through the channel; a first on-off valve that opens and closes the first channel; and a second on-off valve that opens and closes the second channel. The first channel and the second channel are connected to an end portion of the body fluid bag, the end portion being, when mounted on the centrifugal separator, on the side of a direction of centrifugal force by the centrifugal separator.

According to the present invention, the first channel and the second channel are connected to an end portion of the body fluid bag on the side of the direction of centrifugal force. Therefore, the separation layers having a concentration gradient of predetermined cells separated along the direction of centrifugal force by the centrifugal separator can be passed through the filter in order of closeness to the first channel. Accordingly, the separation layers can be passed through the filter in ascending order of the concentration of the predetermined cells. As a result, as compared with the case where a body fluid component having a uniform concentration of cells to be removed is passed through a filter, the efficiency of cell removal by a filter can be increased. In addition, a separation layer containing the second body fluid component other than the separation layers containing the first body fluid component can also be received in the second body fluid component bag using the second channel. In addition, because the first channel and the second channel are connected to an end portion of the body fluid bag on the side of the direction of centrifugal force, using the centrifugal force of the centrifugal separator, it is possible not only to separate the body fluid in the body fluid bag, but also to send a fluid to the body fluid component bag using the first channel or the second channel. Accordingly, the processing time from the body fluid separation to the body fluid component production can be shortened.

The present invention from still another point of view is a cell removal system that is mounted on a centrifugal separator and removes predetermined cells from a body fluid. The cell removal system includes: a body fluid bag that receives a body fluid; a first body fluid component bag that receives a first body fluid component having a relatively high cell concentration in the body fluid; a second body fluid component bag that receives a second body fluid component having a relatively low cell concentration in the body fluid; a first channel that connects the first body fluid component bag and the body fluid bag; a second channel that connects the second body fluid component bag and the body fluid bag; a filter that is provided in the first channel and removes predetermined cells from a body fluid component passing through the channel; a first on-off valve that opens and closes the first channel; and a second on-off valve that opens and closes the second channel. The first channel is connected to an end portion of the body fluid bag, the end portion being, when mounted on the centrifugal separator, on the side of a direction of centrifugal force by the centrifugal separator. The second channel is connected to an end portion of the body fluid bag, the end portion being, when mounted on the centrifugal separator, on the opposite side from the direction of centrifugal force by the centrifugal separator.

According to the present invention, the first channel is connected to an end portion of the body fluid bag on the side of the direction of centrifugal force. Therefore, the separation layers having a concentration gradient of predetermined cells separated along the direction of centrifugal force by the centrifugal separator can be passed through the filter in order of closeness to the first channel. Accordingly, the separation layers can be passed through the filter in ascending order of the concentration of the predetermined cells. As a result, as compared with the case where a body fluid component having a uniform concentration of cells to be removed is passed through a filter, the efficiency of cell removal by a filter can be increased. In addition, a separation layer containing the second body fluid component other than the separation layers containing the first body fluid component can also be received in the second body fluid component bag using the second channel. In addition, because the first channel is connected to an end portion of the body fluid bag on the side of the direction of centrifugal force, using the centrifugal force of the centrifugal separator, it is possible not only to separate the body fluid in the body fluid bag, but also to send the separation layers to the first body fluid component bag using the first channel. Accordingly, the processing time from the body fluid separation to the body fluid component production can be shortened.

It is also possible that an additional filter may be provided in the second channel to remove predetermined cells from a body fluid component passing through the channel. In such a case, predetermined cells can be removed also from a body fluid component having a low cell concentration.

It is also possible that the cell removal system further includes a preservation liquid supply circuit that is provided in the first channel in a position closer to the body fluid bag than the filter and supplies a preservation liquid for preserving the first body fluid component. In such a case, the preservation liquid can be supplied together with the removal of predetermined cells. In addition, a body fluid component passing through the first channel is diluted with the preservation liquid and thus more easily passes through the filter. Therefore, the burden on the filter can be reduced, prolonging the life of the filter.

The predetermined cells may be a disease-causing substance. In addition, it is also possible that the body fluid is blood, the first body fluid component is a blood component containing red blood cells as a main component, the second body fluid component is a blood component containing plasma as a main component, and the predetermined cells may be white blood cells.

The present invention from still another point of view is a method for removing white blood cells from a body fluid containing red blood cells and white blood cells. The method includes: applying centrifugal force to a body fluid placed in a first bag by centrifugal separation to form separation layers containing at least the red blood cells and the white blood cells and having a concentration gradient of the white blood cells; passing the separation layers through a filter in ascending order of the concentration of the white blood cells according to the concentration gradient of the white blood cells to remove the white blood cells from the separation layers; and receiving the separation layers from which the white blood cells have been removed in a second bag.

In the white blood cell removal method, when the separation layers are passed through the filter, a passing rate may be changed according to the concentration of the white blood cells.

According to the present invention, in the removal of predetermined cells from a body fluid, the efficiency of predetermined cell removal by a filter can be improved. In addition, the improvement of the efficiency of predetermined cell removal allows for the reduction of filter size. As a result, the amount of useful components caught by the filter and wasted can be reduced, and the recovery of useful body fluid components can be increased.

DETAILED DESCRIPTION

Figure 1:
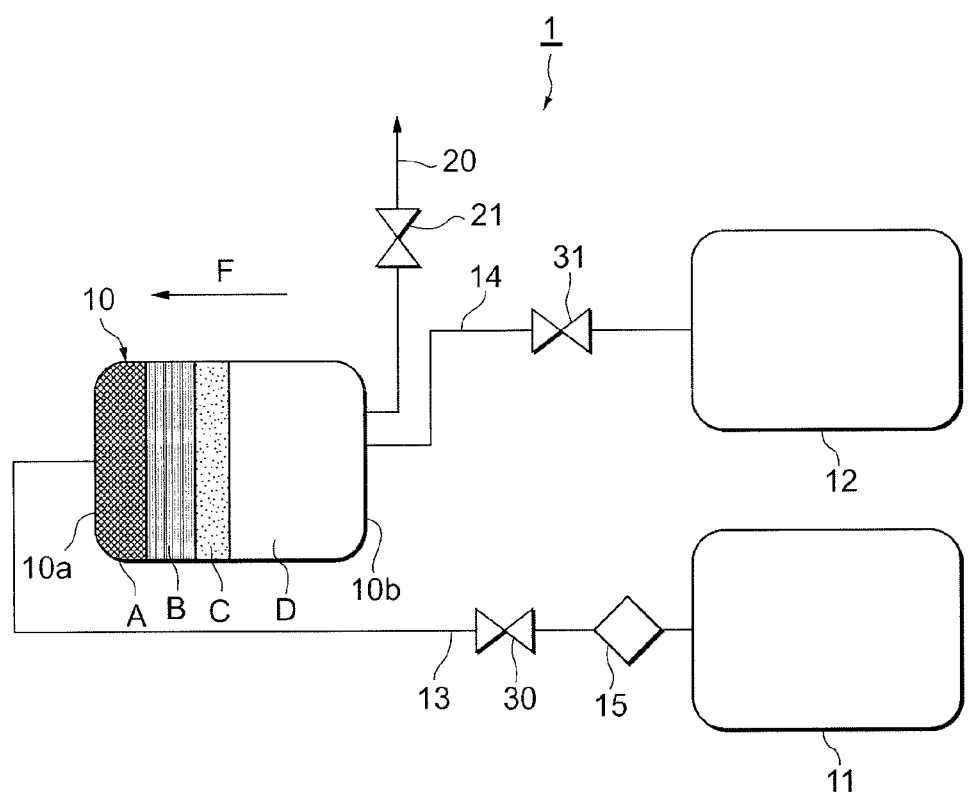
FIG. 1 is an explanatory drawing schematically showing the configuration of a cell removal system.

Hereinafter, a preferred embodiment of the present invention will be described with reference to the drawings. FIG. 1 is an explanatory drawing schematically showing the configuration of a cell removal system 1 according to this embodiment.

The cell removal system 1 can be mounted on a centrifugal separator 2 described below and includes, for example, a blood bag 10 as a first bag, a first blood component bag 11 as a second bag, a second blood component bag 12 as a third bag, a first channel 13, a second channel 14, a filter 15, etc.

The blood bag 10 is made of soft resin, etc., for example, and is deformable. The blood bag 10 has connected thereto a channel 20 for blood collection, and can receive blood collected from the human body. The channel 20 for blood collection has provided therein an on-off valve 21 that opens and closes the channel 20.

The first blood component bag 11 and the second blood component bag 12 are made of soft resin, etc., for example, and are deformable.

As the first channel 13 and the second channel 14, soft tubes are used, for example. The first channel 13 connects the blood bag 10 and the first blood component bag 11. The first channel 13 is connected to, for example, a first end portion 10a of the blood bag 10. The end portion 10a is on the side of the direction of centrifugal force F by the centrifugal separator 2 when the blood bag 10 is mounted on the centrifugal separator 2. The first channel 13 has provided therein a first on-off valve 30 that opens and closes the channel 13.

The second channel 14 connects the blood bag 10 and the second blood component bag 12. The second channel 14 is connected to, for example, a second end portion 10b of the blood bag 10. The end portion 10b is on the opposite side from the direction of centrifugal force F by the centrifugal separator 2 when the blood bag 10 is mounted on the centrifugal separator 2. The second channel 14 has provided in a second on-off valve 31 that opens and closes the channel 14. Incidentally, the channel 20 for blood collection mentioned above is also connected to the second end portion 10b of the blood bag 10.

The filter 15 is provided in the first channel 13. The filter 15 is formed of a porous body, for example, which can filter out white blood cells as predetermined cells, which are pathogens. The filter 15 is provided between the first on-off valve 30 and the first blood component bag 11.

Figure 2:
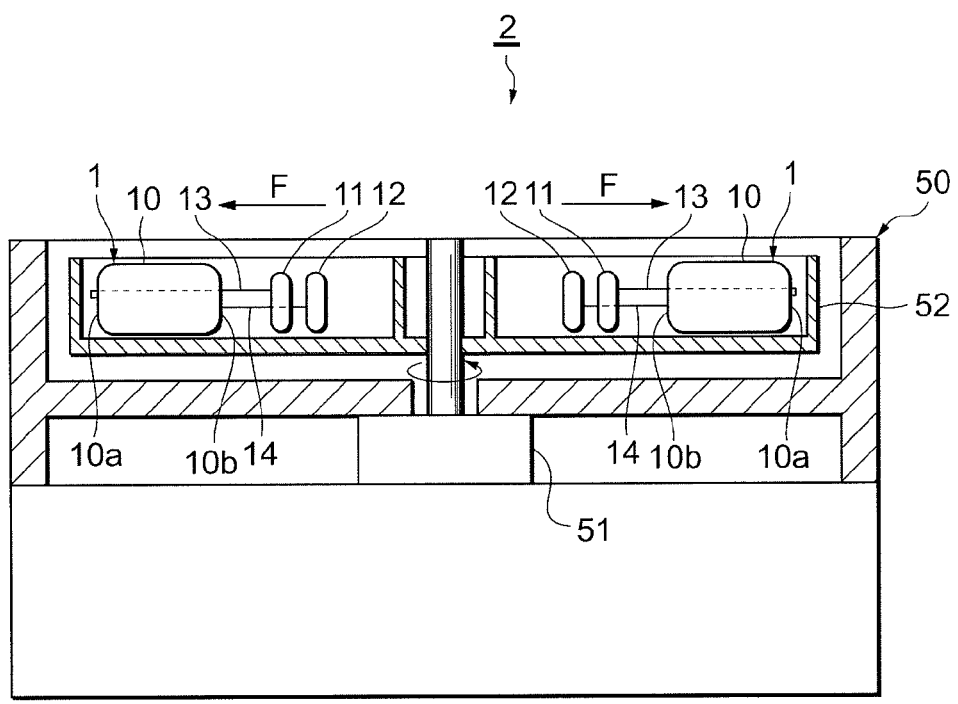
FIG. 2 is a longitudinal sectional view schematically showing the configuration of a centrifugal separator.
Figure 3:
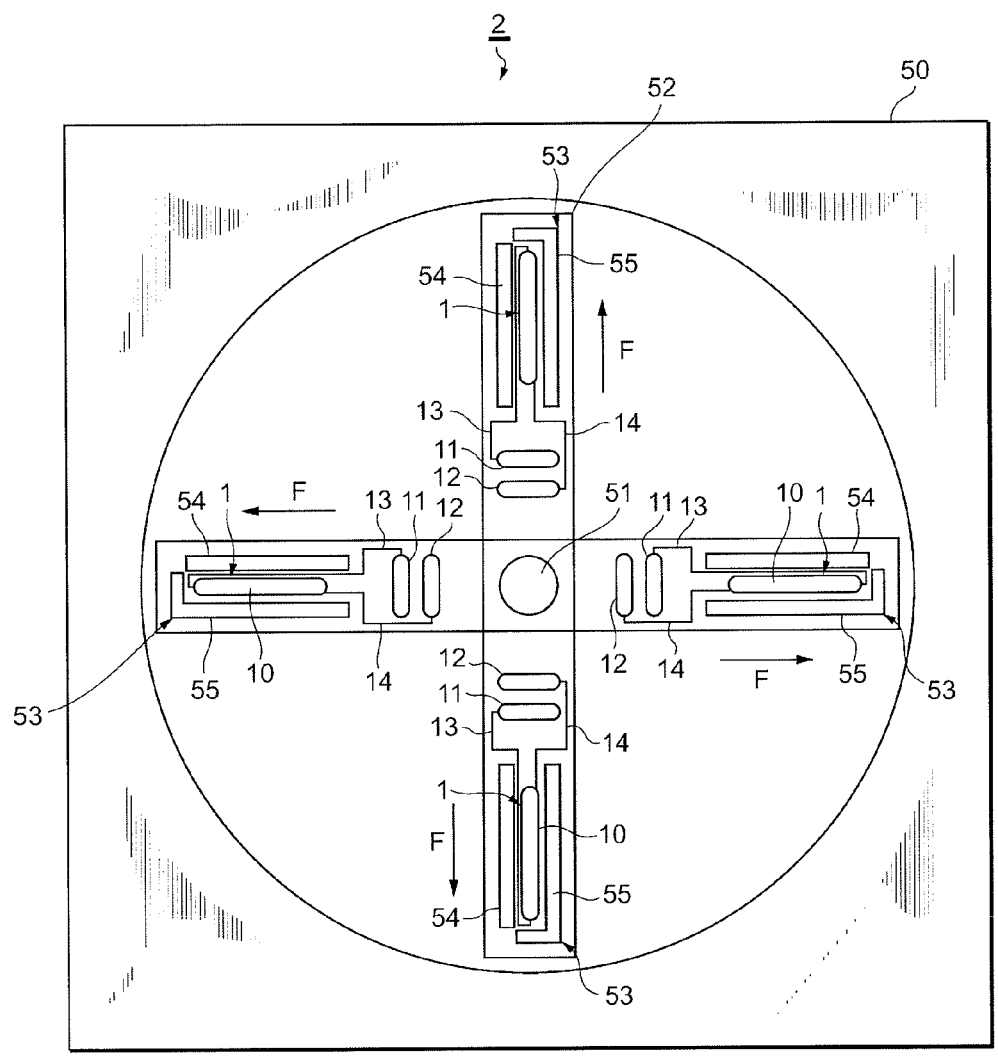
FIG. 3 is a plan view schematically showing the configuration of a centrifugal separator.

The centrifugal separator 2 includes, for example, as shown in FIG. 2 and FIG. 3, in a housing 50, a rotary actuators 51 such as a motor, a rotary container 52 which is rotated by the rotary actuator 51 and on which a plurality of cell removal systems 1 can be mounted, etc. In the rotary container 52, for example, the blood bag 10 of the cell removal system 1 can be installed in such a manner that the first end portion 10a, to which the first channel 13 is connected, faces the outside (the side of the direction of centrifugal force F), while the second end portion 10b, to which the second channel 14 is connected, faces the center (the opposite side from the direction of centrifugal force F). Incidentally, in this embodiment, the blood bag 10 is installed in such a manner that the length direction of the bag (horizontal direction in FIG. 4) is in the direction of centrifugal force F, while the thickness direction of the bag (vertical direction in FIG. 4) is in the direction of rotation.

Figure 4:
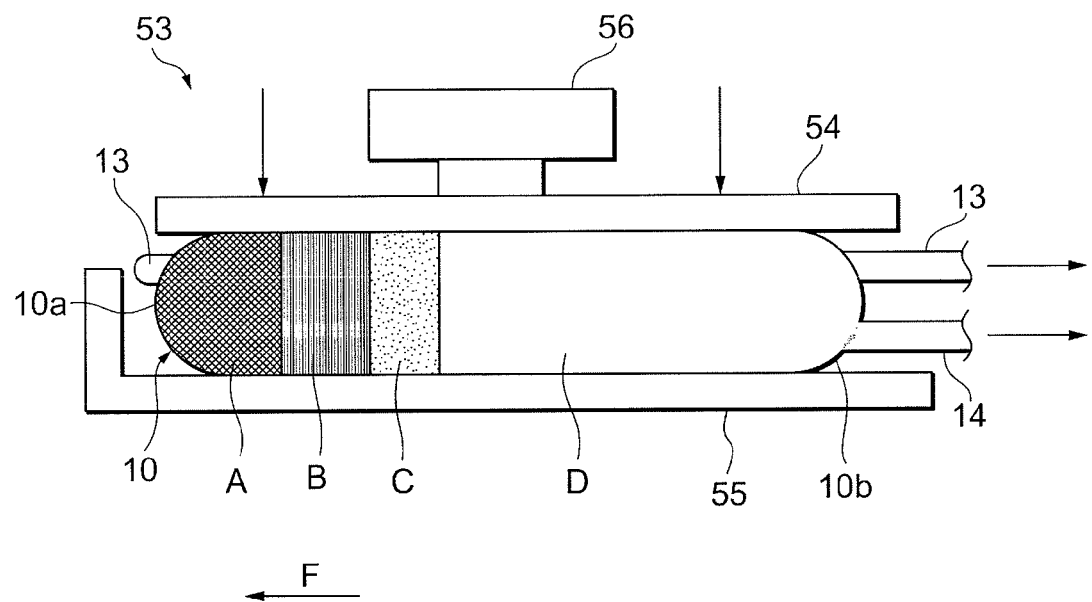
FIG. 4 is an explanatory drawing showing the configuration of a pressing mechanism.

The rotary container 52 is provided with, for example, a pressing mechanism 53 for pressing the blood bag 10 from sides. The pressing mechanism 53 has, for example, as shown in FIG. 4, a pair of pressing plates 54 and 55 that sandwich the blood bag 10 from both sides. One pressing plate 54 can be moved horizontally by a pressing actuator 56 such as a cylinder toward the other pressing plate 55 to press the blood bag 10 therebetween. Blood in the blood bag 10 can thus be pressed out toward the first channel 13 or the second channel 14.

Next, a blood cell removal method using the cell removal system 1 thus configured will be described.

First, blood collected from the human body is introduced through the channel 20 for blood collection and received in the blood bag 10. At this time, the first on-off valve 30 and the second on-off valve 31 are closed. Next, the cell removal system 1 is mounted on the rotary container 52 of the centrifugal separator 2. At this time, the blood bag 10 is, for example, as shown in FIG. 4, installed between the pressing plate 54 and the pressing plate 55 in such a manner that the first end portion 10a faces the side of the direction of centrifugal force F, while the second end portion 10b faces the opposite side from the direction of centrifugal force F.

Next, the centrifugal separator 2 operates such that the rotary container 52 is rotated by the rotary actuator 51, whereby the blood in the blood bag 10 is separated by centrifugal force, along the direction of centrifugal force F, into separation layers A, B, and C having a concentration gradient of leukocyte cells, for example, and a separation layer D as an additional separation layer as shown in FIG. 1. The leukocyte cell concentration increases in order of separation layers C, B, and A (A<B<C), for example. Incidentally, the leukocyte cell concentration of the separation layer D is lower than the separation layer C. The separation layers A, B, and C are component layers containing a large amount of erythrocyte cells and serve as packed cell layers having a relatively high cell concentration. The separation layer D is a component layer containing plasma as a main component and serves as a sparse cell layer having a relatively low cell concentration. In addition, the red blood cell concentration increases in order of separation layers A, B, and C (A>B>C), and the separation layer C contains a large amount of platelets.

Next, the second on-off valve 31 is opened, and the pressing mechanism 53 operates such that the blood bag 10 is pressed by the pressing plates 54 and 55. Accordingly, the separation layer D that is close to the second end portion 10b on the opposite side from the direction of centrifugal force F is pressed out from the blood bag 10, and sent to the second blood component bag 12 through the second channel 14 shown in FIG. 1. Accordingly, a plasma component as a second body fluid component is received in the second blood component bag 12. This serves as a plasma product.

After the entire separation layer D is pressed out from the blood bag 10, next, the second on-off valve 31 is closed, and the first on-off valve 30 is opened. Subsequently, the blood bag 10 is further pressed by the pressing plates 54 and 55, and the separation layers A, B, and C are pressed out into the first channel 13 in order of closeness to the first end portion 10a. Accordingly, they are pressed out into the first channel 13 in ascending order of leukocyte cell concentration, that is, in the following order: separation layers A, B, and C. First, the separation layer A having the lowest leukocyte cell concentration is passed through the filter 15 for the removal of white blood cells, and received in the first blood component bag 11. Next, the separation layer B having the second lowest leukocyte cell concentration is passed through the filter 15 for the removal of white blood cells, and received in the first blood component bag 11. Finally, the separation layer C having the highest leukocyte cell concentration is passed through the filter 15 for the removal of white blood cells, and received in the first blood component bag 11. In this manner, a packed red blood cell component containing red blood cells as a main component is received as a first body fluid component in the first blood component bag 11. This serves as a red blood cell product. Subsequently, the first on-off valve 30 is closed. The process of cell removal from blood is thus completed.

According to above embodiment, by centrifugal force, separation layers A, B, and C having a concentration gradient of white blood cells, which are predetermined cells, are formed, and the separation layers A, B, and C are passed through the filter 15 in ascending order of white blood cell concentration. Thus, the side having the highest white blood cell concentration can be the last to pass through the filter 15. Accordingly, filtration can be continued while suppressing a decrease in the white blood cell removal performance caused by a temporary decrease in the number of adsorption sites accompanying the progress of filtration, which is seen in the case where a body fluid component having a uniform cell concentration is passed through a filter. As a result, the efficiency of white blood cell removal by the filter 15 can be increased.

Incidentally, although the separation layer D is pressed out from the blood bag 10 prior to the separation layers A to C in the above embodiment, it is also possible to press out the separation layer D after the separation layers A to C.

In addition, in the above embodiment, the first channel 13 is connected to the first end portion 10a of the blood bag 10 on the side of the direction of centrifugal force F. Therefore, it is also possible to use the centrifugal force of the centrifugal separator 2 to send the separation layers A to C from the blood bag 10 to the first blood component bag 11. This allows the separation layers A to C to be passed through the filter 15 while reliably maintaining their separation state. In addition, the separation layers A to C can be passed through the filter 15 during or immediately after the centrifugal separation that separates blood into the separation layers A to D, whereby the time of the cell removal process can be shortened.

Figure 5:
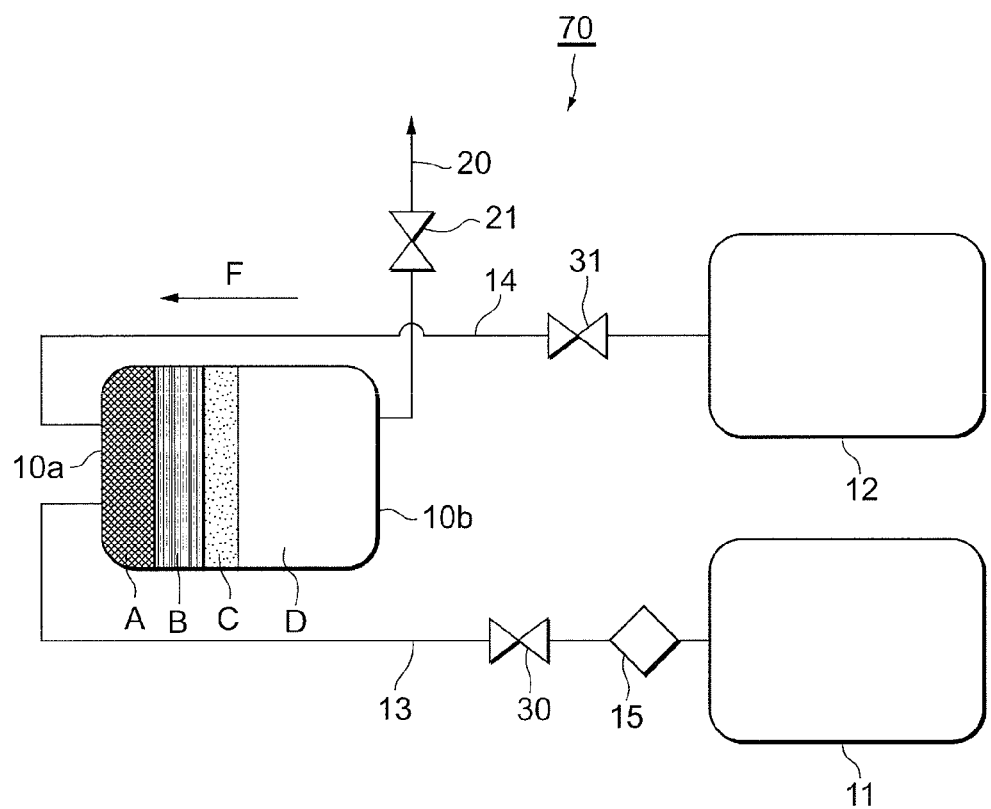
FIG. 5 is an explanatory drawing of a cell removal system in the case where a first channel and a second channel are connected to a first end portion of a blood bag.

In addition, in the above embodiment, it is also possible to use the centrifugal force of the centrifugal separator 2 to send the separation layer D to the second blood component bag 12. In such a case, as shown in FIG. 5, the second channel 14 is connected to the first end portion 10a of the blood bag 10. Then, by the centrifugal force of the centrifugal separator 2, the separation layers A to C are sent to the first blood component bag 11 through the first channel 13, and then the separation layer D is sent to the second blood component bag 12 through the second channel 14. In such a case, the need for a special device for pressing out the separation layers A to D, such as the pressing mechanism 53, is eliminated, whereby the cost of cell removal process can be reduced. In addition, the supply to the blood component bags 11 and 12 can be performed during or following the centrifugal separation of blood, whereby the time of cell removal process can be further shortened.

Figure 6:
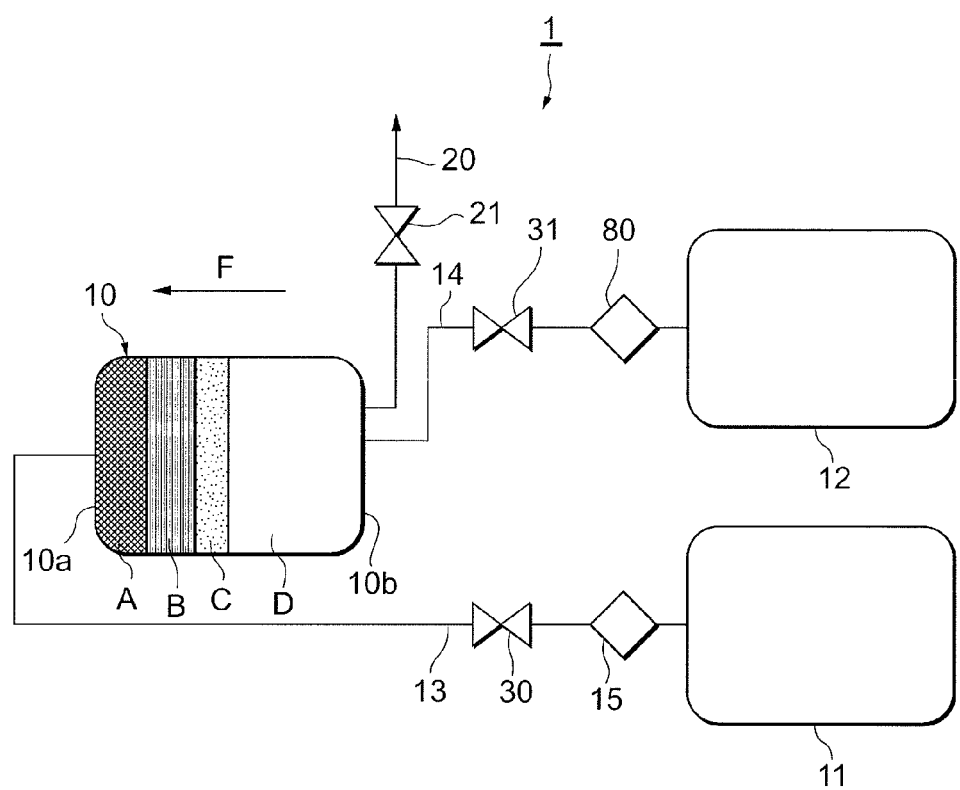
FIG. 6 is an explanatory drawing of a cell removal system in the case where a filter is provided in a second channel.

In the above embodiment, for example, as shown in FIG. 6, it is also possible to provide a filter 80 in the second channel 14 to remove white blood cells, for example, as necessary. In such a case, white blood cells can be removed from the separation layer D by the filter 80 when the separation layer D passes through the second channel 14. Therefore, in the case where the separation layer D contains white blood cells, a plasma product from which white blood cells have been removed can be produced. Incidentally, this example is also applicable to the case where, as shown in FIG. 5, the second channel 14 is connected to the first end portion 10a of the blood bag 10.

Figure 7:
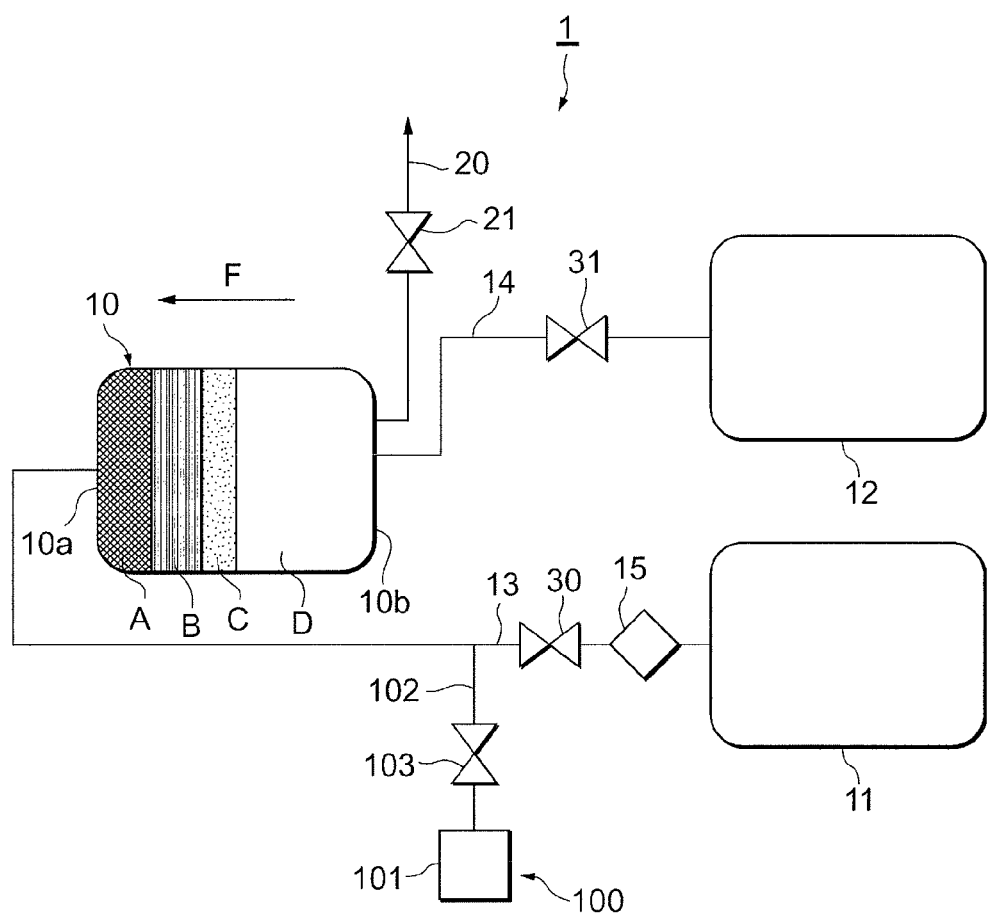
FIG. 7 is an explanatory drawing of a cell removal system in the case where a preservation liquid supply circuit is connected to a first channel.

In the above embodiment, a preservation liquid for preserving the eventually produced red blood cell product may be added to the separation layers A to C before being passed through the filter 15. For example, as shown in FIG. 7, a preservation liquid supply circuit 100 for supplying a preservation liquid is provided in the first channel 13 in a position closer to the blood bag 10 than the filter 15. The preservation liquid supply circuit 100 includes, for example, a preservation liquid bag 101, a preservation liquid supply channel 102 that connects the preservation liquid bag 101 and the first channel 13, and an on-off valve 103 that opens and closes the channel 102. For example, when the separation layers A to C are pressed out from the blood bag 10, the on-off valve 103 is opened, and a preservation liquid is supplied from the preservation liquid bag 101 through the preservation liquid supply channel 102 to the first channel 13. Accordingly, the preservation liquid is added to the blood components of the separation layers A to C flowing through the first channel 13, and then the separation layers A to C pass through the filter 15.

According to this example, the preservation liquid can be added to the red blood cell product at the same time as the white blood cell removal process. In addition, the separation layers A to C are diluted with the preservation liquid and thus more easily pass through the filter 15. Therefore, the burden on the filter 15 can be reduced. Accordingly, the life of the filter 15 can be prolonged. Incidentally, this example is also applicable to the case where, as shown in FIG. 5, the second channel 14 is connected to the first end portion 10a of the blood bag 10.

In the above embodiment, when the separation layers A to C are passed through the filter 15, the passing rate may be changed according to the leukocyte cell concentration. For example, in the case where the separation layers A to C are pressed out toward the filter 15 by the pressing mechanism 53, the rate at which the blood bag 10 is pressed by the pressing plates 54 and 55 of the pressing mechanism 53 may be changed to change the passing rate of each of the separation layers A to C through the filter 15. In the case where the separation layers A to C are pressed out toward the filter 15 using the centrifugal force of the centrifugal separator 2, the centrifugal force may be changed to change the passing rate of each of the separation layers A to C through the filter 15. For example, it is possible that the passing rate is set low when the separation layer C having a high white blood cell concentration passes through the filter 15, the passing rate is set high when the separation layer A having a low white blood cell concentration passes through the filter 15, and the passing rate is set medium when the separation layer B having a medium white blood cell concentration passes through the filter 15. This allows white blood cells to be appropriately removed from each of the separation layers A to C without putting too much burden on the filter 15.

Preferred embodiments of the present invention have been described above with reference to the accompanying drawings, but the invention is not limited to these examples. It is obvious that a person skilled in the art can conceive of various modifications or amendments within the concept defined in the claims, and they are naturally construed as being within the technical scope of the present invention.

Figure 8:
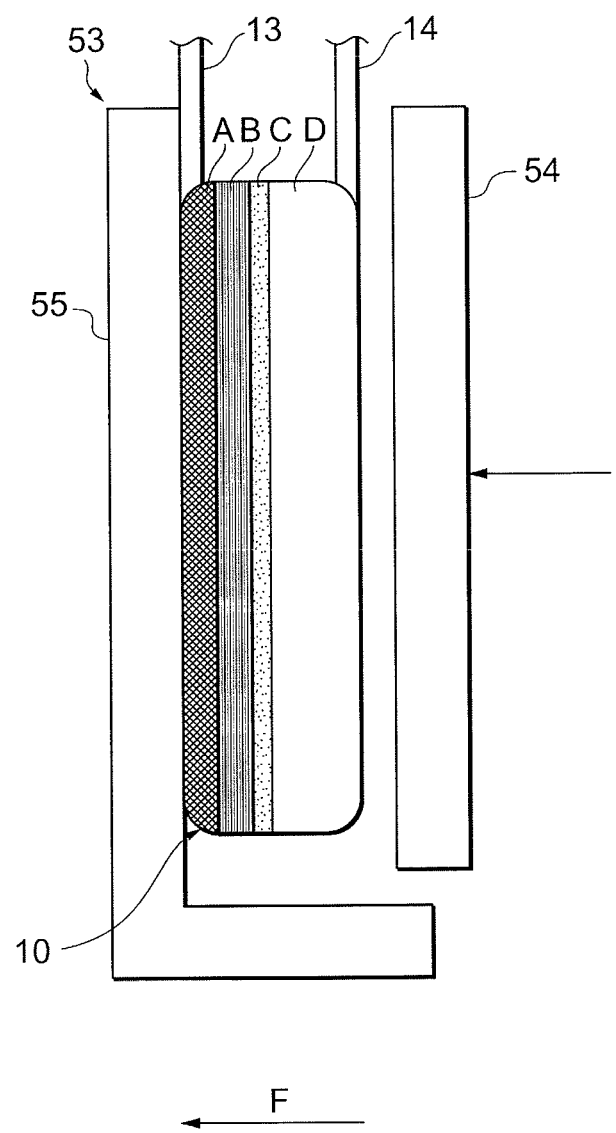
FIG. 8 is an explanatory drawing showing the case where a blood bag is installed in a centrifugal separator in a different direction.

For example, the above embodiment has shown an example where the blood bag 10 is installed in such a manner that the length direction of the bag (vertical direction in FIG. 1) is in the direction of centrifugal force F when the cell removal system 1 is mounted on the centrifugal separator 2. However, as shown in FIG. 8, it is also possible that the blood bag 10 is installed in such a manner that the thickness direction of the bag (horizontal direction in FIG. 8) is in the direction of centrifugal force F. In such a case, the first channel 13 and the second channel 14 are connected to one end portion of the blood bag 10 in the thickness direction. In addition, it is also possible that the pressing mechanism 53 is configured to press the blood bag 10 from sides in the thickness direction thereof.

In the above embodiment, the blood component that undergoes white blood cell removal and is received in the first blood component bag 11 is a red blood cell product. However, it may also be a whole blood product, a platelet product, an intermediate product thereof, etc. For example, in the case of a platelet product, for example, separation layers C and D containing platelets pass through the filter 15 via the first channel 13 in order of separation layers D and C, and a platelet product is received in the first blood component bag 11.

Figure 9:
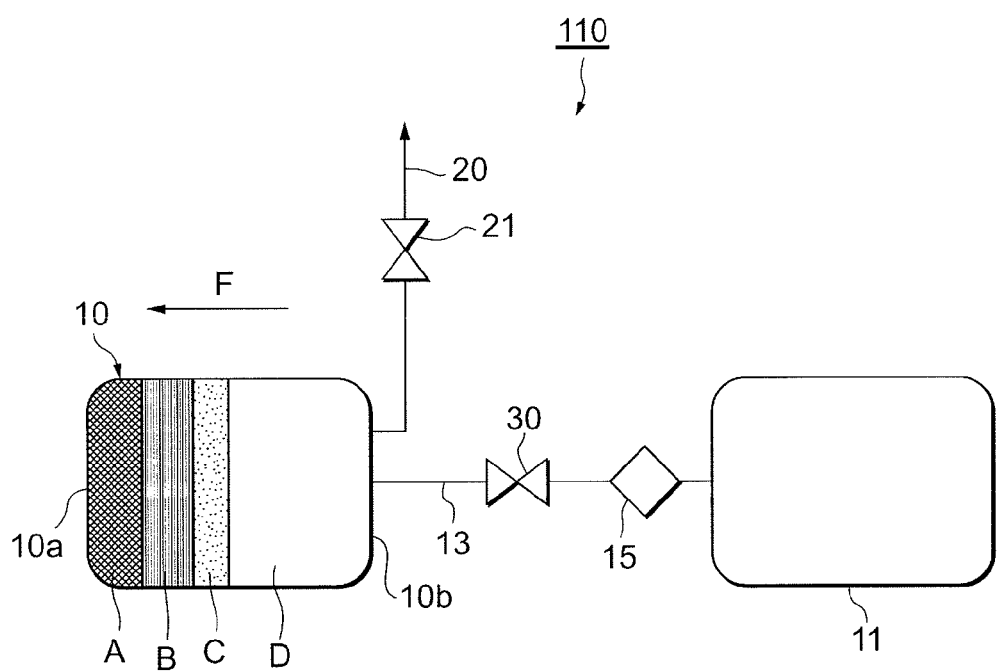
FIG. 9 is an explanatory drawing of a cell removal system in the case of the production of a whole blood product.

In addition, in the case of a whole blood product, although the cell removal system 1 or the like mentioned above may be used, it is also possible to use a cell removal system 110 that has no second channel 14 or second blood component bag 12 but has only the first channel 13 and the first blood component bag 11 as shown in FIG. 9. In such a case, all the separation layers A to D pass through the filter 15 via the first channel 13 in order of separation layer D, C, B, and A, for example, and a whole blood product is received in the first blood component bag 11.

In the above embodiment, four separation layers are mainly present, and three of the separation layers mainly pass through the filter 15 and have a concentration gradient of white blood cells. However, the number of layers is not limited thereto. In addition, cells to be removed are not limited to white blood cells either, and may also be other cells such as platelets and red blood cells. Further, the filter 15 may also be capable of removing other disease-causing substances such parasites in addition to pathogenic substances such as white blood cells. In addition, the body fluid from which cells are removed is blood in the above embodiment, but the present invention is also applicable to the cases of other body fluids such as bone marrow and umbilical cord blood.

EXAMPLES

Hereinafter, the results of experiments for the evaluation of the removal performance of a filter will be shown.

The method for preparing a filter used in the experiments is as follows.

(1) Production of Filter Medium:

The following polymer was used as a material for a filter.

Random polymer of 2-hydroxyethyl methacrylate (HEMA) and dimethylaminoethyl methacrylate (DM) (the molar ratio between HEMA and DM=97:3, hereinafter abbreviated as "HM-3").

At a monomer concentration in ethanol of 1 mol/L, HM-3 was synthesized by random polymerization at 60° C. for 8 hours in the presence of 0.005 mol/L of 2,2'-azobis(2,4-dimethylvaleronitrile) (manufactured by Wako Pure Chemical Industries, Ltd. trade name: V-65) as an initiator.

First, HM-3 was dissolved in a water/ethanol mixed solvent (the weight ratio of water/ethanol=5/95) to prepare a 0.1 wt % solution. The following nonwoven fabrics A and B were impregnated with this solution and, after the removal of excess liquid, vacuum-dried at 40° C. for 16 hours.

A: Polyester nonwoven fabric having an average fiber diameter of 1.8 μm produced by melt-blowing B: Polyester nonwoven fabric having an average fiber diameter of 1.2 μm produced by melt-blowing (2) Production of Filter In a container having an effective filtration area of 67 mm×67 mm, the HM-3-coated polyester nonwoven fabric having an average fiber diameter of 1.8 μm produced by melt-blowing was placed so that the pack density was 0.18 g/cm$^3$ and the thickness was 1.5 mm, and similarly the polyester nonwoven fabric having an average fiber diameter of 1.2 μm was placed thereunder so that the pack density was 0.2 g/cm$^3$ and the thickness was 3 mm.

Example 1

The blood centrifugal filtration method of Example 1 using the above filter is as follows.

(1) From a healthy individual, 250 mL of fresh whole blood having added thereto CPD (Citrate Phosphate Dextrose) was collected in a blood bag (hereinafter referred to as "whole blood").

(2) The whole blood was transferred to a 250-mL bottle for centrifugation, placed in a centrifugal cup, and then subjected to centrifugation at 1250 G for 5 minutes. The bottle for centrifugation was then taken out from the centrifugal cup.

(3) In the bottle, about 140 mL of a packed red blood cell layer and about 110 mL of a platelet-rich plasma layer had been formed.

(4) About 110 mL of the platelet-rich plasma layer was sucked and recovered in a bottle. At this time, suction was performed carefully in order not to affect the interface with the packed red blood cell layer.

(5) Then, 35 mL of the packed red blood cell layer remaining in the bottle was carefully collected by suction from the upper part to give a first layer of the packed red blood cell fluid. The concentration of white blood cells (measured using a microcell counter) was $469 \times 10e^2/\mu L$, the hematocrit was 30.5%, and the concentration of platelets was $29.1 \times 10e^4/\mu L$.

(6) Further, 35 mL of the packed red blood cell layer remaining in the bottle was carefully collected by suction from the upper part to give a second layer of the packed red blood cell fluid. The concentration of white blood cells was $141 \times 10e^2/\mu L$, the hematocrit was 53.5%, and the concentration of platelets was $9.1 \times 10e^4/\mu L$.

(7) Next, 30 mL of the packed red blood cell layer remaining in the bottle was collected from the upper part and mixed with 5 mL of a SAGM liquid (red blood cell preservation liquid) to give 35 mL of a third layer of the packed red blood cell fluid. The concentration of white blood cells was $22 \times 10e^2/\mu L$, the hematocrit was 60.2%, and the concentration of platelets was $4 \times 10e^4/\mu L$. Incidentally, from the dilution ratio, before the addition of the SAGM liquid, the white blood cell concentration was $26 \times 10e^2/\mu L$, the hematocrit was 70.2%, and the platelet concentration was $5 \times 10e^4/\mu L$.

(8) Next, 26 mL of the packed red blood cell layer remaining in the bottle was collected from the upper part and mixed with 9 mL of a SAGM liquid to give 35 mL of a fourth layer of the packed red blood cell fluid. The concentration of white blood cells was $9.3 \times 10e^2/\mu L$, the hematocrit was 61.3%, and the concentration of platelets was $2 \times 10e^4/\mu L$. Incidentally, from the dilution ratio, before the addition of the SAGM liquid, the white blood cell concentration was $12.5 \times 10e^2/\mu L$, the hematocrit was 82.5%, and the platelet concentration was $3 \times 10e^4/\mu L$.

(9) Next, 18 mL of the packed red blood cell layer remaining in the bottle was collected from the upper part and mixed with 8 mL of a SAGM liquid to give 26 mL of a fifth layer of the packed red blood cell fluid. The concentration of white blood cells was $7.6 \times 10e^2/\mu L$, the hematocrit was 60.5%, and the concentration of platelets was $1 \times 10e^4/\mu L$. Incidentally, from the dilution ratio, before the addition of the SAGM liquid, the white blood cell concentration was $11.0 \times 10e^2/\mu L$, the hematocrit was 87.4%, and the platelet concentration was $1 \times 10e^4/\mu L$.

(10) A five-port flexible pipe made of polyvinyl chloride was connected to the inlet side of the white blood cell removal filter. A similar pipe having a blood bag for recovery connected to its end was connected to the outlet side of the filter. The first to fifth layers of the packed red blood cell fluid were transferred to five 50-mL-volume syringes, respectively, and the syringes were connected to five connecting ports of the pipe, respectively. The syringes were subjected to thorough mixing by inversion so that the packed red blood cell fluid in each syringe was made uniform, and then installed in a syringe pump set at a flow rate of 20 mL/min.

(11) The syringe pump was switched on for the syringe containing the fifth layer of the packed red blood cell fluid, whereby the fifth layer was sent to start filtration through the filter. When the fifth layer of the packed red blood cell fluid disappeared from the syringe, then the fourth layer of the packed red blood cell fluid was sent. Subsequently, the third layer, the second layer, and the first layer of the packed red blood cell fluid were sequentially sent. In this manner, in order from the fifth layer having a low white blood cell concentration to the first layer having a high white blood cell concentration, the layers were sent, passed through the filter, and recovered in the blood bag for recovery.

(12) The amount of the packed red blood cell fluid eventually recovered in the blood bag for recovery was 145 mL. Sampling after mixing showed that the concentration of white blood cells (counted using a flow cytometer) was 3.01 cells/$\mu L$ and the hematocrit was 57.6%, while no platelets were detected. The total number of white blood cells in the eventually recovered 145 mL of the packed red blood cell fluid that had undergone white blood cell removal was $0.44 \times 10e^6$.

Comparative Example 1

The blood centrifugal filtration method of Comparative Example 1 using the above filter is as follows.

(1) From a healthy individual, 250 mL of whole blood having added thereto CPD was collected in a blood bag.

(2) The whole blood was transferred to a 250-mL bottle for centrifugation, placed in a centrifugal cup, and then subjected to centrifugation at 1250 G for 5 minutes. The bottle for centrifugation was then taken out from the centrifugal cup.

(3) In the bottle, about 140 mL of a packed red blood cell layer and about 110 mL of a platelet-rich plasma layer had been formed.

(4) About 110 mL of the platelet-rich plasma layer was sucked and recovered in a bottle. At this time, suction was performed carefully in order not to affect the interface with the packed red blood cell layer.

(5) A 22-mL quantity of a SAGM liquid was added to the packed red blood cell layer remaining in the bottle and then uniformly mixed to prepare 162 mL of a packed red blood cell fluid. The concentration of white blood cells was $132 \times 10e^2/\mu L$, the hematocrit was 53.7%, and the concentration of platelets was $27.3 \times 10e^4/\mu L$. As a result of calculation, the total number of white blood cells in 162 mL of the prepared packed red blood cell fluid was $2.1 \times 10e^9$.

(6) The packed red blood cell fluid was dispensed into four 35-mL syringes and one 22-mL syringe. A five-port flexible pipe made of polyvinyl chloride was connected to the inlet side of a white blood cell removal filter produced in the same manner as in Example 1. A similar pipe having a blood bag for recovery connected to its end was connected to the outlet side. Subsequently, the syringes were connected to five connecting ports of the pipe, respectively. The syringes were subjected to thorough mixing by inversion so that the packed red blood cell fluid in each syringe was made uniform, and then installed in a syringe pump set at a flow rate of 20 mL/min. The white blood cell concentration of the packed red blood cell fluid is the same in all the syringes.

(7) The syringe pump was switched on for the first syringe containing the packed red blood cell fluid, whereby the packed red blood cell fluid was sent to start filtration through the filter. When the packed red blood cell fluid disappeared from the first syringe, then the sending of the fluid in the second syringe was started. In this manner, the packed red blood cell fluid of each of the five syringes was passed through the filter and recovered in the blood bag for recovery.

(8) The amount of the packed red blood cell fluid eventually recovered in the blood bag for recovery was 145 mL. Sampling after mixing showed that the concentration of white blood cells (counted using a flow cytometer) was 7.46 cells/$\mu L$ and the hematocrit was 53.7%, while no platelets were detected. The total number of white blood cells in the eventually recovered 145 mL of the packed red blood cell fluid that had undergone white blood cell removal was $1.08 \times 10e^6$.

Comparative Example 2

The blood centrifugal filtration method of Comparative Example 2 using the above filter is as follows.

(1) From a healthy individual, 250 mL of whole blood having added thereto to CPD was collected in a blood bag.

(2) The whole blood was transferred to a 250-mL bottle for centrifugation, placed in a centrifugal cup, and then subjected to centrifugation at 1250 G for 5 minutes. The bottle for centrifugation was then taken out from the centrifugal cup.

(3) In the bottle, about 140 mL of a packed red blood cell layer and about 110 mL of a platelet-rich plasma layer had been formed.

(4) About 110 mL of the platelet-rich plasma layer was sucked and recovered in a bottle. At this time, suction was performed carefully in order not to affect the interface with the packed red blood cell layer.

(5) Then, 35 mL of the packed red blood cell layer remaining in the bottle was carefully collected by suction from the upper part to give a first layer of the packed red blood cell fluid. The concentration of white blood cells (measured using a microcell counter) was $469 \times 10e^2/\mu L$, the hematocrit was 30.5%, and the concentration of platelets was $29.1 \times 10e^4/\mu L$.

(6) Further, 35 mL of the packed red blood cell layer remaining in the bottle was carefully collected by suction from the upper part to give a second layer of the packed red blood cell fluid. The concentration of white blood cells was $141 \times 10e^2/\mu L$, the hematocrit was 53.5%, and the concentration of platelets was $9.1 \times 10e^4/\mu L$.

(7) Next, 30 mL of the packed red blood cell layer remaining in the bottle was collected from the upper part and mixed with 5 mL of a SAGM liquid (red blood cell preservation liquid) to give 35 mL of a third layer of the packed red blood cell fluid. The concentration of white blood cells was $22 \times 10e^2/\mu L$, the hematocrit was 60.2%, and the concentration of platelets was $4 \times 10e^4/\mu L$. Incidentally, from the dilution ratio, before the addition of the SAGM liquid, the white blood cell concentration was $26 \times 10e^2/\mu L$, the hematocrit was 70.2%, and the platelet concentration was $5 \times 10e^4/\mu L$.

(8) Next, 26 mL of the packed red blood cell layer remaining in the bottle was collected from the upper part and mixed with 9 mL of a SAGM liquid to give 35 mL of a fourth layer of the packed red blood cell fluid. The concentration of white blood cells was $9.3 \times 10e^2/\mu L$, the hematocrit was 61.3%, and the concentration of platelets was $2 \times 10e^4/\mu L$. Incidentally, from the dilution ratio, before the addition of the SAGM liquid, the white blood cell concentration was $12.5 \times 10e^2/\mu L$, the hematocrit was 82.5%, and the platelet concentration was $3 \times 10e^4/\mu L$.

(9) Next, 18 mL of the packed red blood cell layer remaining in the bottle was collected from the upper part and mixed with 8 mL of a SAGM liquid to give 26 mL of a fifth layer of the packed red blood cell fluid. The concentration of white blood cells was $7.6 \times 10e^2/\mu L$, the hematocrit was 60.5%, and the concentration of platelets was $1 \times 10e^4/\mu L$. Incidentally, from the dilution ratio, before the addition of the SAGM liquid, the white blood cell concentration was $11.0 \times 10e^2/\mu L$, the hematocrit was 87.4%, and the platelet concentration was $1 \times 10e^4/\mu L$.

(10) A five-port flexible pipe made of polyvinyl chloride was connected to the inlet side of the white blood cell removal filter. A similar pipe having a blood bag for recovery connected to its end was connected to the outlet side of the filter. The first to fifth layers of the packed red blood cell fluid were transferred to five 50-mL-volume syringes, respectively, and the syringes were connected to five connecting ports of the pipe, respectively. The syringes were subjected to thorough mixing by inversion so that the packed red blood cell fluid in each syringe was made uniform, and then installed in a syringe pump set at a flow rate of 20 mL/min.

(11) The syringe pump was switched on for the syringe containing the first layer of the packed red blood cell fluid, whereby the first layer was sent to start filtration through the filter. When the first layer of the packed red blood cell fluid disappeared from the syringe, then the second layer of the packed red blood cell fluid was sent. Subsequently, the third layer, the fourth layer, and the fifth layer of the packed red blood cell fluid were sequentially sent. In this manner, in order from the first layer having a high white blood cell concentration to the fifth layer having a low white blood cell concentration, the layers were sent, passed through the filter, and recovered in the blood bag for recovery.

(12) The amount of the packed red blood cell fluid eventually recovered in the blood bag for recovery was 145 mL. Sampling after mixing showed that the concentration of white blood cells (counted using a flow cytometer) was 38.2 cells/$\mu L$ and the hematocrit was 58.7%, while no platelets were detected. The total number of white blood cells in the eventually recovered 145 mL of the packed red blood cell fluid that had undergone white blood cell removal was $5.54 \times 10e^6$.

The present invention is useful in improving the efficiency of predetermined cell removal by a filter in the separation of a predetermined body fluid component from a body fluid.

1: Cell removal system
2: Centrifugal separator
10: Blood bag
10$a$: First end portion
10$b$: Second end portion
11: First blood component bag
12: Second blood component bag
13: First channel
14: Second channel
15: Filter
30: First on-off valve
31: Second on-off valve
A to D: Separation layer
F: Direction of centrifugal force

We claim:

1. A method for removing predetermined cells from a body fluid, the method comprising:
  applying centrifugal force to the body fluid placed in a first bag by centrifugal separation to form separation layers having a concentration gradient of the predetermined cells,
  providing a force generating member that comprises: at least one of a centrifugal separator that produces the centrifugal force and a press that applies a pressure to the first bag;
  passing the separation layers through a filter in ascending order of the concentration of the predetermined cells according to the concentration gradient of the predetermined cells to remove the predetermined cells from the separation layers; and
  receiving the separation layers from which the predetermined cells have been removed in a second bag;
  wherein, when the separation layers are passed through the filter, one of the centrifugal force and the pressure generated by the force generating member is changed so as to regulate and change a passing rate of each of the separation layers being passed through the filter according to a concentration of the predetermined cells in the separation layers having the concentration gradient of the predetermined cells.

2. The method for removing predetermined cells according to claim 1, wherein a predetermined body fluid component produced by removing the predetermined cells from the separation layers is received in the second bag, and a preservation liquid for preserving the body fluid component is added to the separation layers before being passed through the filter.

3. The method for removing predetermined cells according to claim 1, wherein an additional separation layer, other than the separation layers, is separated by the centrifugal force and is received in a third bag separately from the separation layers.

4. The method for removing predetermined cells according to claim 1, wherein the predetermined cells are pathogens.

5. The method for removing predetermined cells according to claim 1, wherein the body fluid is blood, the predetermined cells are white blood cells, and the predetermined cells are removed from the separation layers to produce a blood component containing red blood cells as a main component.

6. The method for removing predetermined cells according to claim 1, wherein the one of the centrifugal force and pressure is regulated such that the passing rate of the separation layer having a relatively high concentration of the predetermined cells is set relatively low and the passing rate of the separation layer having a relatively low concentration of the predetermined cells is set relatively high.

* * * * *